(12) United States Patent
Chen et al.

(10) Patent No.: US 7,556,795 B2
(45) Date of Patent: Jul. 7, 2009

(54) RADIOPHARMACEUTICAL FORMULATIONS

(75) Inventors: Jianqing Chen, Bordentown, NJ (US); Karen E. Linder, Kingston, NJ (US); Nannan Wang, No. Brunswick, NJ (US); Aldo Cagnolini, Edison, NJ (US)

(73) Assignee: Bracco Imaging S.p.A., Milan (IT)

( * ) Notice: Subject to any disclaimer, the term of this patent is extended or adjusted under 35 U.S.C. 154(b) by 592 days.

(21) Appl. No.: 10/513,586

(22) PCT Filed: May 5, 2003

(86) PCT No.: PCT/US03/13936

§ 371 (c)(1), (2), (4) Date: May 16, 2005

(87) PCT Pub. No.: WO03/092743

PCT Pub. Date: Nov. 13, 2003

(65) Prior Publication Data

US 2006/0034760 A1 Feb. 16, 2006

Related U.S. Application Data

(60) Provisional application No. 60/377,454, filed on May 3, 2002.

(51) Int. Cl.
*A61K 51/00* (2006.01)
*A61M 36/14* (2006.01)

(52) U.S. Cl. .......... 424/1.69; 424/1.11; 424/1.65; 424/1.49

(58) Field of Classification Search ........... 424/1.11, 424/1.65, 1.49, 1.37, 1.69, 1.73, 9.1, 9.3, 424/9.4, 9.5, 9.6, 9.7, 9.8; 534/7, 10–16
See application file for complete search history.

(56) References Cited

U.S. PATENT DOCUMENTS 6,200,546 B1    3/2001    Hoffman
RE37,710 E      5/2002    McBride et al.
6,916,460 B2 *  7/2005    Liu .............................. 424/9.3
7,060,247 B2 *  6/2006    Hoffman et al. ............. 424/9.1

OTHER PUBLICATIONS

Valliant et al (Inorganica Chimica Acta, 2001, vol. 325, pp. 155-163).*
International Preliminary Examination Report for PCT/US03/13936 mailed Dec. 10, 2004.
PCT International Search Report for PCT/US03/13936, Aug. 22, 2003.
Van de Wiele, et al. "Technetium-99m RP527, a GRP analouge for visulisation of GRP receptor-expressing malignancies: a feasibility study" European Journal of Nuclear Medicine, vol. 27, No. 11, Nov. 2000.
Kasina, S., et al., "Simplified Preformed Chelate Protein Radiolabelling with Technetium-99M Mercaptoacetamidoadipolyglycylglycine (N3S-Adipate)" Bioconjugate Chemistry, ACS, Washington, DC, vol. 9, No. 1, Jan. 1, 1998, pp. 108-117, XP000729236.
Pearson, Daniel A., et al., "Somatostatin Receptor-Binding Peptides Labeled with Technetium-99M: Chemistry and Initial Biological Studies" Journal of Medicinal Chemistry, vol. 39, No. 7, Mar. 29, 1996, pp. 1361-1371, XP002513683.
Hoffman, T.J., et al., "Radiometallated receptor-avid peptide conjugates for specific in vivo targeting of cancer cells" Nuclear Medicine and Biology, Elsevier, NY, vol. 28, No. 5, Jul. 1, 2001, pp. 527-539, XP004247061.
Supplementary European Search Report of European Application No. EP03733935, mailed Feb. 12, 2009.

* cited by examiner

*Primary Examiner*—D. L Jones
(74) *Attorney, Agent, or Firm*—Kramer, Levin, Naftlais & Frankel LLP (57) ABSTRACT

Radiopharmaceutical compounds are disclosed having a radionuclide chelating moiety and a targeting ligand, and optionally a linker. Formulations of compositions useful for making the radiopharmaceutical compounds contain a chelating ligand, a reducing agent, an exchange ligand and a stabilizer.

31 Claims, 1 Drawing Sheet

TcOMe₂N-Gly-Ser-Cys—Gly-5-aminovaleroyl—Gln-Trp-Ala-Val-Gly-His-Leu-Met-NH₂

Radiometal Chelation　　　　　Linker　　　　　Receptor Binding Site
Moiety

FIG. 1

RADIOPHARMACEUTICAL FORMULATIONS

This application is the national stage application of corresponding international application number PCT/US03/13936 filed May 5, 2003 which claims priority to and the benefit of U.S. Provisional Application No. 60/377,454, filed May 3, 2002, all of which are hereby incorporated by reference.

FIELD OF THE INVENTION

The invention relates to formulations for radiopharmaceuticals comprising radionuclide chelators.

BACKGROUND OF THE INVENTION

Targeted radiopharmaceuticals resolve an image of diagnostic interest or deliver a therapeutic radioisotope to an area of interest by binding or localizing selectively to a site within the body. For various diagnostic and therapeutic applications, chelators that bind a metal radionuclide and are linked to a targeting molecule have been employed with varying degrees of success. Such chelators often have a region incorporating four or more donor atoms that form five- or six-membered rings appropriate for high affinity radionuclide binding. Typical metal radionuclides used for diagnostic imaging agents include $^{99m}Tc$, $^{64}Cu$, $^{67}Cu$, $^{97}Ru$, $^{109}Pd$, $^{198}Au$, $^{199}Au$, $^{111}In$, in their various chlorides, oxides or nitrides. Typical metal radionuclides used for radiotherapeutic applications include $^{186}Re$, $^{188}Re$, $^{111}In$, $^{166}Ho$, $^{105}Rh$, $^{149}Pm$, $^{153}Sm$, $^{177}Lu$, $^{90}Y$, $^{203}Pb$, $^{212}Pb$ and $^{212}Bi$ in their various chlorides, oxides or nitrides. Numerous types of molecules have been employed as targeting molecules, including polyclonal and monoclonal antibodies and fragments thereof, proteins and peptides, especially those capable of binding with specificity to cell surface receptors (generally referred to as "receptor-binding ligands"). When labeling peptide and protein-based targeting agents, the chelator is ideally also peptide-based, so that the chelator-targeting molecule conjugate can be synthesized using peptide synthesis techniques. For example, U.S. Pat. Nos. 5,662,885; 5,780,006; and 5,976,495 (each of which is incorporated herein by reference in its entirety) disclose chelators that bind metal radionuclides, can be coupled to targeting agents capable of localizing at body sites of diagnostic and therapeutic interest, and are peptide analogs designed structurally to present an $N_3S$ configuration capable of binding oxo, dioxo and nitrido ions of, for example, $^{99m}Tc$ and $^{186/188}Re$. Moreover, peptidic cores that chelate isotopes of Tc and other diagnostic and therapeutic radionuclides are known; most of this work has focused on using peptides derived from natural amino acids of the form $NH_2CHRCOOH$.

Despite the many advances in diagnostic imaging, several obstacles are routinely encountered in this field. One of the key problems is the development of useful formulations for the preparation of the targeted radiopharmaceutical. One problem frequently encountered is that many formulations require a high concentration of the targeted chelating ligand in reactions for the preparation of a targeted radiopharmaceutical to assure high yields of the desired complex. These formulations produce radiopharmaceutical preparations with significant amounts of "free" targeted chelating ligand that has not been chelated to the radiometal. For many applications this "free" ligand is undesirable; thus, it must be separated from the labeled ligand using chromatographic techniques such as High Pressure Liquid Chromatography (HPLC) prior to further use. This is often necessary where the targeting molecule attached to the chelator is, for example, an agonist, and exhibits biological activity when it binds to a target receptor. Such biological activity is undesirable in a diagnostic compound and may also be undesirable in a therapeutic one. In addition, receptor-binding ligands that are not complexed with a radionuclide may compete at the target receptor with those ligands that are complexed with a radionuclide, resulting in poor targeting of the radionuclide complex and poor diagnostic or therapeutic characteristics.

Figure 1:
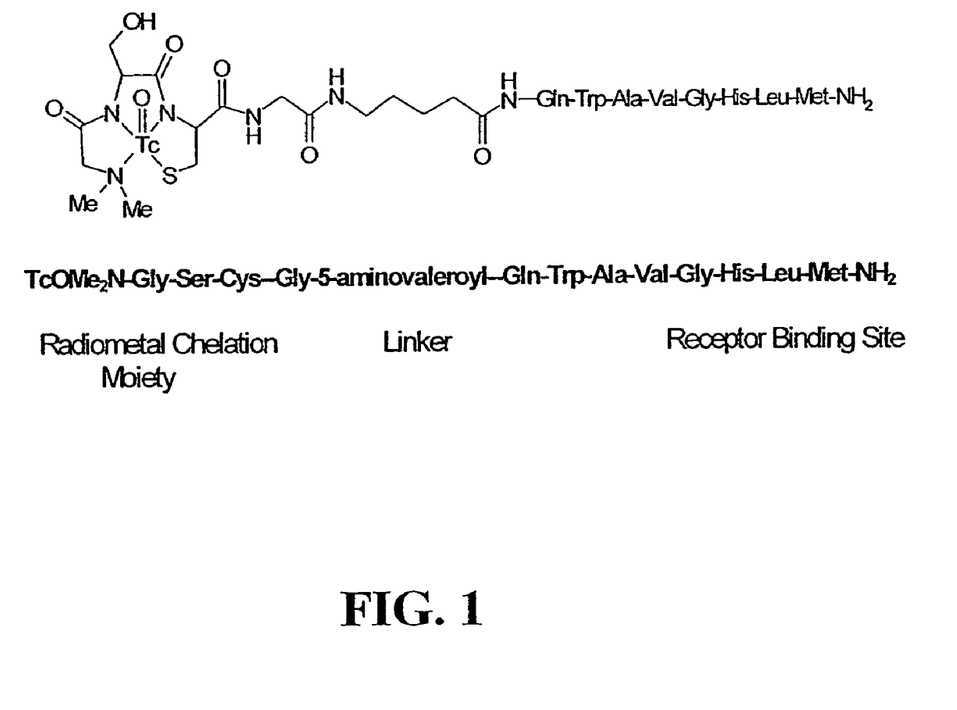
FIG. 1 shows the chemical structure of the $^{99m}$Tc complex of Compound 1, a preferred targeted chelating ligand used in formulations of the present invention.

The targeted radiopharmaceutical with the structure shown in FIG. 1 is an example. The uncomplexed receptor binding ligand (or targeted chelating ligand) used to make this complex contains a tripeptide $N_3S$ chelator [(N-(Me$_2$)-Gly-Ser-Cys(Acm)] that forms a complex with Tc(V)O, losing the acetamidomethyl (Acm) protecting group in the process. The chelator sequence is linked to the N-terminus of an octapeptide targeting molecule, pGlu-Trp-Ala-Val-Gly-His-Leu-Met-NH$_2$ derived from bombesin, via a linker of Gly-aminovaleric acid. Both this ligand and the Tc complex formed from it are agonists that are known to bind to Gastrin Releasing Peptide (GRP) Receptors with high affinity. See, e.g., U.S. Pat. No. 6,200,546, which is hereby incorporated by reference in its entirety. Clinical studies that were performed with this compound, e.g. those described by Van de Wiele et al. (European Journal of Nuclear Medicine, Vol. 27, No. 11, 2000 p. 1694 (which is hereby incorporated by reference in its entirety) were prepared using the following prototype 4-vial kit. To each of 2 vials, each containing 100 µg of ligand was added 0.1 mL of stannous chloride (2 mM), 0.1 mL of sodium gluconate (60 mM), 1850-2035 MBq (50-55 mCi) of $^{99m}TcO_4^-$ in 0.3 mL of 0.9% sodium chloride, and 0.5 mL of sodium chloride. After 35 min. in a boiling water bath, the pooled reaction mixtures were injected on an HPLC system and purified in order to separate labeled from unlabelled peptide, followed by terminal sterilization. The overall yield from this radiosynthesis was ~30%, with a radiochemical purity after purification of >90%. The purified compound could be stored at 4° C. for only up to 2 hours. This procedure, although useful to provide initial evidence of the potential clinical utility of the compound, is not commercially viable because it uses a 4-vial frozen kit, requires preparative HPLC (i.e., instrumentation that is not typically available in nuclear medicine units) to remove excess ligand prior to injection, and does not provide a sterile product except by terminal sterilization. In addition, it uses >100 mCi of $^{99m}TcO_4^-$ to make a patient dose, requires the use of generator eluant that is 2 hours old or less, and the purified product can only be used for 2 hours after isolation.

It would be highly advantageous to have a formulation for the preparation of this and other receptor-binding targeted radiopharmaceuticals that, among other things, can be used clinically (e.g., directly injected) without the need for HPLC purification. The present invention addresses this need and other problems in the art.

SUMMARY OF THE INVENTION

The present invention features radiopharmaceutical formulations useful in diagnostic imaging and/or radiotherapy. In one aspect, the invention features radiopharmaceutical formulations containing targeted chelating ligands having the structure of Formula I:

wherein $R^1$ is H or is a linear or branched, saturated or unsaturated C1-4 alkyl chain that is optionally interrupted by one or two heteroatoms selected from N, O and S; and is optionally substituted by at least one group selected from halogen, hydroxyl, amino, carboxyl, C1-4 alkyl, aryl and C(O)Z;

$R^2$ is a substituent defined by $R^1$; or $R^1$ and $R^2$ may together form a 5- to 8-membered saturated or unsaturated heterocyclic ring optionally substituted by at least on group selected from halogen, hydroxyl, amino, carboxyl, C1-4 alkyl, aryl and C(O)Z;

$R^3$ is —H, —$CH_2OH$, or -t-butyl;

L is optional and is a linking group; and

Z is a targeting molecule.

In preferred embodiments, the formulation comprises compositions in which both $R^1$ and $R^2$ are methyl. In a more preferred embodiment both $R^1$ and $R^2$ are methyl and Z is a bombesin analog, most preferably a bombesin analog that is an agonist, such as those disclosed in U.S. Pat. No. 6,200,546, incorporated by reference herein in its entirety.

Unlike many prior compositions for the preparation of targeted radiopharmaceuticals, the radiopharmaceutical formulations of the invention utilize a small amount of chelator/targeting molecule conjugate (e.g., compounds of Formula I). Indeed, in a preferred embodiment, radiopharmaceutical formulations of the invention are provided that contain between about 2 to about 10 μg of a targeted chelating ligand of Formula 1, thus reducing the risk of unwanted biological activity or physiological effects resulting from the administration of, e.g., a biologically active peptide.

The radiopharmaceutical formulations of the invention further include the components described in detail herein (e.g. reducing agent, exchange ligand, stabilizer, solubilizer, diluent, etc.) In a preferred embodiment, the formulation of the invention includes Compound 1, $SnCl_2.2H_2O$, gluconic acid (sodium salt), gentisic acid (sodium salt), ethanol and optionally hydroxypropyl-γ-cyclodextrin, or pharmaceutically acceptable salts thereof.

The invention also encompasses kits for the preparation of targeted radiopharmaceuticals that contain the radiopharmaceutical formulations of the invention. Preferred kits include the uncomplexed targeted chelating ligand, the reducing agent, the exchange ligand, the stabilizer(s) and any solubilizers in one or more vials, and the diluent in a separate vial. A particularly preferred kit of the invention includes two vials. The first vial comprises: Compound 1, $SnCl_2.2H_2O$, gluconic acid (sodium salt), gentisic acid (sodium salt), and optionally hydroxypropyl-γ-cyclodextrin. The second vial comprises ethanol, and optionally water and/or normal saline.

In a preferred embodiment, radiopharmaceutical formulations of the invention have a radiochemical purity value (RCP) that is greater than or equal to 90% within 15 min. after reconstitution. In another preferred embodiment, radiopharmaceutical formulations of the invention have a radiochemical purity value that is greater than or equal to 90% at six hours after reconstitution. Radiopharmaceuticals prepared from formulations of the invention may be injected directly into a subject without any purification. In addition, such radiopharmaceuticals may be prepared at room temperature.

DETAILED DESCRIPTION OF THE INVENTION

Radiopharmaceutical formulations of the present invention have significant advantages over previous formulations. These formulations contain significantly less targeted chelator than prior art formulations. Indeed the formulations of the invention contain less than 10 μg of targeted chelator per mL of diluent. Preferably, a radiopharmaceutical formulation of the invention contains less than about 5 μg of targeted chelator per mL of diluent. Most preferably, a radiopharmaceutical formulation of the invention contains about 4 μg of targeted chelator per mL of diluent, with a total reconstitution volume between about 0.5 mL and about 1 mL, most preferably 1.0 mL. In particular, the present invention provides radiopharmaceutical formulations that may be prepared and administered to a subject without any purification. In addition, the radiopharmaceutical formulations of the invention have a radiochemical purity (RCP) of greater than or equal to 90% at about 15 minutes after preparation (i.e., reconstitution). Most preferred radiopharmaceutical formulations of the invention have a RCP that is greater than or equal to about 90% at about six hours after preparation.

The diluent used to reconstitute the radiopharmaceutical formulations of the present invention may be any combination of water, normal saline and/or ethanol. Preferably, the diluent is a mixture of water, normal saline and ethanol in which the percentage of ethanol ranges from about 20% to about 40% (v/v), most preferably about 30%. The pH of the formulation after reconstitution is between 2.8 and 4.0, most preferably about pH 3.0.

Radiopharmaceuticals of the present invention may be prepared by a reaction with a reducing agent able to reduce the radionuclide (which is in an oxidized state) to a reduced state that can coordinate with the ligand, such as a stannous source, sodium borohydride, Cu(I) salts, formamidine sulphinic acid and the like. The preferred reductant is a stannous salt such as stannous chloride, stannous fluoride, stannous tartrate and the like. Stannous chloride (as $SnCl_2.2H_2O$) is most preferred. The reducing agent is present at a concentration of about 20 to about 60 μg/mL, most preferably about 40 μg/mL.

The formulation of the present invention preferably contains one or more stabilizers chosen from maltose, ascorbic acid, gentisic acid or pharmaceutically acceptable salts of these acids. The sodium salt of gentisic acid is most preferred. This reagent is preferably present at a concentration of about 10 to about 25 mg/mL, most preferably 20 mg/mL.

An exchange ligand is preferably present in the formulation of the present invention to help stabilize Tc in a reduced oxidation state until such time as it has chelated to the desired targeted chelating ligand. Such exchange ligands can include, for example, gentisic acid, gluconate, or glucoheptonate, or pharmacologically acceptable salts of these compounds. Sodium gluconate is most preferred. The exchange ligand is present at a concentration of about 1 to about 3 mg/mL, most preferably 1.3 mg/mL.

A detergent is optionally present in the formulation of the present invention to help improve recovery of the radioactive product from the vial. Such detergents can include non-ionic, cationic, anionic and zwitterionic surfactants including, for example, sodium dodecyl sulfate, N-dodecyl sulaine, Tween™ 80, cetyltrimethylammonium bromide, cyclo-n-methyl-β-D-malloside and n-hexyl-β-D-glucopyranoside. Non-ionic detergents are particularly preferred, with cyclo-n-methyl-β-D-malloside and n-hexyl-β-D-glucopyranoside especially preferred. Detergent may be present in an amount in the range of about 5-100 mg/ml, preferably about 100 mg/ml.

Typical metal radionuclides used for diagnostic imaging agents include $^{99m}$Tc, $^{64}$Cu, $^{67}$Cu, $^{97}$Ru, $^{109}$Pd, $^{198}$Au, $^{199}$Au, $^{111}$In, in their various chlorides, oxides or nitrides. Typical metal radionuclides used for radiotherapeutic applications include $^{186}$Re, $^{188}$Re, $^{111}$In, $^{166}$Ho, $^{105}$Rh, $^{149}$Pm, $^{153}$Sm, $^{177}$Lu, $^{90}$Y, $^{203}$Pb, $^{212}$Pb, $^{212}$Bi and the radioactive actinides and additional radioactive lanthanides in their various chlorides, oxides or nitrides. The preferred radioisotope used for the preparation of radiopharmaceuticals made with the present formulation are isotopes of technetium and rhenium (e.g., $^{94}$Tc, $^{99m}$Tc, $^{186}$Re, $^{188}$Re). Most preferably, the isotope used is $^{99m}$Tc as a pertechnetate salt, $^{99m}$TcO$_4^-$. Between about 5 and about 100 mCi of $^{99m}$Tc can be added, most preferably between about 20 and about 40 mCi.

The radiopharmaceutical formulation of the present invention can be used to prepare radiopharmaceuticals that are reconstituted with radioisotope at any temperature between room temperature and 100° C. When prepared at room temperature, the optimal reaction time is between about 10 and about 60 min, more preferably between about 15 and 30 minutes and most preferably for about 15 min. If prepared by heating to 100° C., optimal yield of the desired complex (>90% RCP) is obtained when kits are heated for about 5 minutes to about 30 min, most preferably between about 5 to about 15 min.

Solubilization aids, such as cyclodextrins (e.g. alpha, beta or gamma cyclodextrin or hydroxypropyl-γ-cyclodextrin) can optionally be present in the formulations of the present invention. Gamma cyclodextrins are preferred, and hydroxypropyl-γ-cyclodextrin is most preferred. The concentration of cyclodextrin may be from about 0.1 to about 10 mg/mL, preferably between about 2.5 and about 5 mg/mL.

As shown in FIG. 1, the radiopharmaceuticals of the invention have two or three domains: a radiometal chelation moiety or chelating core, a linker or linking group (when present), and a receptor binding site or targeting molecule. Together, the chelation moiety and targeting molecule, with or without a linker, may be referred to as a chelating ligand. Compound 1, a preferred ligand for making radiopharmaceutical formulations of the invention, has the following structure:

Compound 1

The synthesis of trifluoroacetic acid and acetic acid salts of Compound 1 is described in Example 1. Example 2 describes the preparation of Compound 1 complexed with $^{99m}$Tc. In Example 3, the effect of the chelating core, namely the NMe$_2$-Gly-Ser-Cys portion of the ligand was examined by modifying the structure of this chelating core. In particular, Compounds 2-4 were synthesized as part of an experiment to examine the effect of the chelating core on RCP:

Compound 2

-continued

Compound 3

Compound 4

The results, described in Example 3 and shown in Table 3, demonstrate that the radiopharmaceutical formulation containing Compound 1 exhibits superior RCP (i.e., greater than 90%), as compared to formulations containing Compounds 2-4.

Example 4 describes one embodiment of a kit for preparing a radiopharmaceutical formulation of the invention and its use for preparing a technetium complex of Compound 1. Examples 5-12 describe synthesis and comparative testing of radiopharmaceutical compounds using detergents, rather than the diluent ethanol.

Targeting Molecules

Any molecule that specifically binds or reactively associates or complexes with a receptor or other receptive moiety associated with a given target cell population may be used as a targeting molecule in radiopharmaceutical formulations of the invention. This cell reactive molecule, to which the metal radionuclide chelation moiety is linked optionally via a linking group, may be any molecule that binds to, complexes with or reacts with the cell population sought to be bound or localized to. The cell reactive molecule acts to deliver the radiopharmaceutical to the particular target cell population with which the molecule reacts. The targeting molecule may be non-peptidic such as, for example, steroids, carbohydrates, lectins or small non-peptidic molecules. The targeting molecule may also be an antibody, such as, for example, a monoclonal or polyclonal antibody or a fragment thereof. Preferably the targeting molecule is a peptide, peptide mimetic or peptoid. Most preferably the targeting molecule is a peptide. Peptides which are useful as targeting molecules include: bombesin, gastrin, gastrin-releasing peptide, transferrin, epidermal growth factors ("EGF"), platelet-derived growth factor, tumor growth factors ("TGF"), such as TGF-α and TGF-β, vaccinia growth factor ("VGF"), insulin and insulin-like growth factors I and II, urotensin II peptides and analogs, NP-Y peptides, octreotide, depreotide, vapreotide, vasoactive intestinal peptide (VIP), cholecystokinin (CCK), insulinlike growth factor (IGF), peptides targeting receptors which are upregulated in angiogenesis such as VEGF receptors (e.g. KDR, NP-1, etc.), RGD-containing peptides, melanocyte-stimulating hormone (MSH) peptide, neurotensin, calcitonin, peptides from complementarity determining regions of an antitumor antibody, glutathione, YIGSR (leukocyte-avid peptides, e.g., P483H, which contains the heparin-binding region of platelet factor-4 (PF-4) and a lysine-rich sequence), atrial natriuretic peptide (ANP), β-amyloid peptides, delta-opioid antagonists (such as ITIPP(psi)), annexin-V, endothelin, IL-1/IL-1ra, IL-2, IL-6, IL-8, leukotriene B4 (LTB4), chemotactic peptides (such as N-formyl-methionyl-leucyl-phenylalanine-lysine (fMLFK)), GP IIb/IIIa receptor antagonists (such as DMP444), epidermal growth factor, human neutrophil elastase inhibitor (EPI-HNE-2, HNE2, and HNE4), plasmin inhibitor, antimicrobial peptides, apticide (P280), P274, thrombospondin receptor (including analogs such as TP-1300), bitistatin, pituitary adenyl cyclase type I receptor (PAC1), and analogs and conservative substitutions of these peptides.

In preferred embodiments, the targeting molecule used in a radiopharmaceutical formulation of the invention is a biologically active peptide. Most preferred embodiments of the present invention include a peptide that binds to a gastrin releasing peptide receptor (GRP-r) and particularly a bombesin analog that is an agonist, such as those disclosed in U.S. Pat. No. 6,200,546. Examples of such peptides are shown in Table 1. Other bombesin analogs, fragments or peptidomimetics may also be used as targeting molecules. For example, NAc-BBN[7-14] has been identified as the minimum fragment that retains both nanomolar binding affinity and elicits biological activity. However, there are a few specific amino acid substitutions in the bombesin 7-14 amino acid binding region (e.g. D-Ala[11] for L-Gly[11] or D-Trp[8] for L-Trp[8]) which can be made without decreasing binding affinity or changing the compound from an agonist to an antagonist. For example, the presence of methionine (Met) at position BBN-14 will generally confer agonistic properties while the deletion of this residue generally confers antagonist properties [R. Camble, et al. Life Science (1989) 45(17), 1521-7].

Furthermore, there is a tolerance to diverse functionalities when chelates, solubilizing groups or linkers are attached at the N-terminus of the 7-14 amino acid residue of bombesin. When bombesin or a bombesin analog is used as the biologically active peptide in a radiopharmaceutical formulation of the invention, the radiopharmaceutical may be targeted to tissue, particularly cancer cells, that express GRP receptors.

TABLE 1

Amino Acid sequences of some natuxal bombesin-like peptides

| Name | Sequence | |
|---|---|---|
| Bombesin (BBN) | PGlu-Gln-Arg-Leu-Gly-Asn-Gln-Trp-Ala-Val-Gly-His-Leu-Met-NH$_2$ | (SEQ ID NO:1) |
| Alytesin | PGlu-Gly-Arg-Leu-Gly-Thr-Gln-Trp-Ala-Val-Gly-His-Leu-Met-NH$_2$ | (SEQ ID NO:2) |
| H-GRP | Val-Pro-Leu-Pro-Ala-Gly-Gly-Gly-Thr-Val-Leu-Thr-Lys-Met-Tyr-Pro-Arg-Gly-Asn-His-Trp-Ala-Val-Gly-His-Leu-Met-NH$_2$ | (SEQ ID NO:3) |
| Litorin | PGlu-Gln-Trp-Ala-Val-Gly-His-Phe-Met-NH$_2$ | (SEQ ID NO:4) |
| Ranatensin | PGlu-Val-Pro-Gln-Trp-Ala-Val-Gly-His-Phe-Met-NH$_2$ | (SEQ ID NO:5) |
| Human neuromedin B | Ala-Pro-Leu-Ser-Trp-Asp-Leu-Pro-Glu-Pro-Arg-Ser-Arg-Ala-Ser-Lys-Ile-Arg-Val-His-Ser-Arg-Oly-Asn-Leu-Trp-Ala-Thr-Gly-His-Phe-Met-NH$_2$ | (SEQ ID NO:6) |
| Phyllolitorin | PGlu-Leu-Trp-Ala-Val-Gly-Ser-Phe-Met-NH$_2$ | (SEQ ID NO:7) |

Linking Groups

The terms "spacer," "spacer group," "linker," and "linking group" are used synonymously herein to refer to a chemical group that serves to couple the targeting molecule to the metal chelator while not adversely affecting either the targeting function of the targeting molecule or the metal complexing function of the metal chelator. Suitable spacer groups include peptides (i.e., amino acids linked together) alone, a non-peptide group (e.g., hydrocarbon chain) or a combination of an amino acid sequence and a non-peptide spacer. A pure peptide spacer consists of a series of amino acids (e.g., diglycine, triglycine, Gly-Gly-Glu, Gly-Ser-Gly, etc.), in which the total number of atoms between the N-terminal residue of the BBN binding moiety and the metal chelator in the polymeric chain is less than or equal to 12 atoms.

The spacer may also include a hydrocarbon chain (i.e., —$R_1$—$(CH_2)_n$—$R_2$—) wherein n is 0-10, preferably n=3 to 9, $R_1$ is a derivative of a group (e.g., $H_2N$—, HS—, —COOH) that can be used as a site for covalently linking the ligand backbone or the preformed metal chelator or metal complexing backbone; and $R_2$ is a group that is used for covalent coupling to the N-terminal $NH_2$-group of the methods for conjugating ligands (i.e., chelators) or preferred metal chelates to biomolecules have been described in the literature. See e.g., Wilbur (1992) *Bioconj. Chem.*, 3: 433; Parker (1990) *Chem. Soc. Rev.,* 19: 271; Hermanson (1996) In: Bioconjugate Techniques, Academic Press, pp. 3-136; Fritzberg et al. (1995) *Radiolabeling of antibodies for targeted diagnostics*. In: Targeted Delivery of Imaging Agents (ed) V. P. Torchilin, CRC Press, Boca Raton, Fla., pp. 84-101 (each of which is hereby incorporated by reference in its entirety). One or more of these methods may be used to link either the uncomplexed ligand (chelator) or the radiometal chelate to the spacer group or to link the spacer group to the targeting molecule. These methods include the formation of acid anhydrides, aldehydes, arylisothiocyanates, activated esters, or N-hydroxysuccinimides. A preferred linking group is -Gly-5-aminovaleric acid-. Additional linkers suitable for use in the subject invention are disclosed in copending patent application U.S. Ser. No. 60/439,722, filed Jan. 13, 2003 and U.S. Ser. No. 10/341,577, filed Jan. 13, 2003, the entire contents of which are hereby incorporated by reference.

Preparation of Radiopharmaceuticals and the Other Formulation Components

The present invention also provides stabilized formulations of radiopharmaceuticals containing the appropriate and usual additives such as buffers, bulling agents, etc. In another embodiment, the present invention may also include single and/or multi-dose kits for preparing radiopharmaceuticals using the formulations of the invention. All non-radioactive reagents of the formulation may be formulated together in a single vial or the complexing ligand may be present in one vial while the stannous or other reducing source may be present in a second vial. In another embodiment, the kit may include a transfer (or trans-chelating) ligand and stannous or other reducing agent in the first vial and the complexing ligand in the second vial. In a further embodiment, the kit formulations may include the usual additives and bulking agents known to those skilled in the art. Methods of reconstituting the kits with radioisotopes are well known to those skilled in the art.

Kits of the present invention comprise one or more vials containing the sterile formulation of a predetermined amount of a complexing ligand, and optionally other components such as reducing agents, transfer ligands, buffers, lyophilization aids or bulking agents, stabilization aids, solubilization aids, bacteriostats and diluents. The inclusion of one or more optional components in the formulation will frequently improve the ease of synthesis of the radiopharmaceutical by the practicing end user, the ease of manufacturing the kit, the shelf-life of the kit, or the stability and shelf-life of the radiopharmaceutical. The improvement achieved by the inclusion of an optional component in the formulation must be weighed against the added complexity of the formulation and added cost to manufacture the kit. The one or more vials that contain all or part of the formulation can independently be in the form of a sterile solution or a lyophilized solid.

Buffers useful in the preparation of radiopharmaceuticals and in diagnostic kits useful for the preparation of the radiopharmaceuticals include but are not limited to phosphate, citrate, sulfosalicylate, and acetate. A more complete list can be found in the United States Pharmacopeia.

Lyophilization aids or bulking agents may optionally be used in the radiopharmaceutical formulations of the invention. Lyophilization and bulking agent are known in the art and include mannitol, lactose, sodium chloride, maltose, sucrose, PEG 8000, cyclodextrins, such as hydroxypropyl-γ-cyclodextrin (HP-γ-CD), dextran, Ficoll, and polyvinylpyrrolidine (PVP). Of these, sodium chloride, maltose, HP-γ-CD, and dextran are preferred bulking agents for use with the invention, with HP-γ-CD being the most preferred.

Stabilization aids or stabilizers useful in the radiopharmaceutical formulations of the invention include but are not limited to ascorbic acid, para-aminobenzoic acid (PABA), sodium bisulfite, sodium metabisulfite, gentisic acid, t-butanol and inositol. Gentisic acid is the most preferred stabilization aid.

Solubilization aids useful in the preparation of radiopharmaceuticals and in diagnostic kits useful for the preparation of the radiopharmaceuticals include but are not limited to ethanol, glycerin, polyethylene glycol, propylene glycol, polyoxyethylene sorbitan monooleate, sorbitan monooloeate, polysorbates, poly(oxyethylene)poly(oxypropylene) poly(oxyethylene) block copolymers (Pluronics) and lecithin. The preferred solubilizing aid is ethanol.

As noted above, a detergent is optionally present in the formulation of the present invention to help improve recovery of the radioactive product from the vial. Such detergents can include non-ionic, cationic, anionic and zwitterionic surfactants including, for example, sodium dodecyl sulfate, N-dodecyl sulaine, Tween™ 80, cetyltrimethylammonium bromide, cyclo-n-methyl-β-D-malloside and n-hexyl-β-D-glucopyranoside. The latter two components are especially preferred. Detergent may be present in an amount in the range of about 5-100 mg/ml, preferably about 100 mg/ml.

Bacteriostats useful in the preparation of radiopharmaceuticals and in diagnostic kits useful for the preparation of the radiopharmaceuticals include but are not limited to benzyl alcohol, benzalkonium chloride, chlorbutanol, and methyl, propyl or butyl parabens.

A component in a diagnostic kit can also serve more than one function. A reducing agent can also serve as a stabilization aid, a buffer or a stabilizer can also serve as a transfer ligand, a lyophilization aid can also serve as a transfer, ancillary or co-ligand and so forth.

In a preferred embodiment the kit of the invention includes: a targeted chelating ligand of the structure shown in Formula I; a stannous salt such as stannous chloride, fluoride or tartrate; a stabilizing aid such as gentisic acid or a pharmaceutically acceptable salt thereof; an exchange ligand such as gluconic acid or a pharmaceutically acceptable salt thereof; and a solubilizing agent such as ethanol and/or a cyclodextrin such as hydroxypropyl gamma cyclodextrin. Most preferably, the kit includes one or two vials. In a particularly preferred embodiment, the kit includes two vials, the first vial containing 4 μg of Compound 1 (triflate or acetate salt); 40 μg of $SnCl_2.2H_2O$; 1.3 mg of Gluconic acid, sodium salt; 20 mg of gentisic acid, sodium salt; and optionally 2.5 mg of hydroxypropyl-γ-cyclodextrin, with the pH of the formulation adjusted to a pH of about pH 3-4 using a pharmacologically acceptable acid or base such as HCl or NaOH; the second vial contains ethanol.

The following abbreviations are used in the examples: TFA, trifluoroacetic acid; HOBt, 1-hydroxybenzotriazole; DIC, N,N'-diisopropylcarbodiimide; HATU, O-(7-azabenzotriazol-1-yl)-1,1,3,3-tetramethyluronium hexafluorophosphate; DIEA, diisopropylethylamine; DMF, dimethylformamide; DMSO, methyl sulfoxide; $CH_2Cl_2$, methylene chloride; EtOH, ethanol. RCP, radiochemical purity; HPLC, high pressure liquid chromatography. Unless otherwise noted, all materials were purchased from Aldrich and used without further purification. Fmoc-5-amino-valeric acid (5-ava) was purchased from Chem-Impex International. All Fmoc-amino acids were purchased from Novabiochem.

EXAMPLE 1

Solid Phase Peptide Synthesis of Compound 1

-continued

Compound 1 was prepared as both its TFA and acetate salt using solid phase peptide synthesis (SPPS), following the procedure described below. Unless otherwise noted, all materials were purchased from Aldrich and used without further purification.

Synthesis of the TFA Salt of Compound 1:

As shown in Scheme 1 above, synthesis of the compound was carried out in dimethyl formamide (DMF) using HOBt/DIC activation on rink-amide Novagel resin. Fmoc deprotection was carried out with 20% piperidine in DMF. The resin was swelled in DMF for 1 h before use. All couplings were of 2 hours duration except for the last N,N-dimethylglycine coupling (see below). A ninhydrin test was employed to determine reaction completion.

A typical coupling cycle is as follows: To a 50-mL SPPS reaction vessel containing 1.13 mmol of the swelled resin (0.6 mmol/g, Novabiochem) was added a solution of 4.52 mmol of an Fmoc-amino acid in DMF (EM Science), 4.52 mmol of HOBT (Novabiochem) in DMF, and 4.52 mmol of DIC. The total volume of DMF was 20 mL. The reaction mixture was shaken for 2 h. The resin then was filtered and washed with DMF (3×30 mL). A ninhydrin test was carried out to confirm the completion of the coupling. A solution of 20% piperidine in DMF (20 mL) was added to the resin and it was shaken for 10 min. The resin was filtered and this piperidine treatment was repeated. The resin was finally washed with DMF (3×30 mL) in preparation for the next coupling cycle.

At the last coupling cycle, N,N-dimethyl glycine was coupled using HATU/DIEA activation. Thus, to a suspension of N,N-dimethyl glycine (4.52 mmol) in DMF was added a solution of 4.52 mmol of HATU (Perseptive Biosystems) in DMF and 9.04 mmol of DIEA. The clear solution was added to the resin and shaken for 16 h. Following synthesis, the resin was washed with DMF (3×30 mL) and $CH_2Cl_2$ (3×30 mL). It was dried by blowing $N_2$ through the container for 15 min. 30 mL of reagent B (TFA/phenol/$H_2O$/triisopropylsilane/methyl sulfide 86 mL/5 g/5 mL/2 mL/2 mL) was added and it was shaken for 4 h. The resin was filtered and the filtrate was evaporated to a paste. The crude peptide was precipitated in diethyl ether and washed twice with ether. 1.2 g of the crude material was obtained after drying. The peptide was purified using Shimadzu HPLC system and a YMC C-18 preparative column. Crude material was dissolved in 15% $CH_3CN/H_2O$ (0.1% TFA) and loaded on the column. The gradient consisted of an increase from 15% to 19% $CH_3CN/H_2O$ (0.1% TFA) in 4 min., followed by 19% to 49% in 60 min. The fractions were combined and lyophilized. A total of 840 mg of the pure material was obtained.

Synthesis of the Acetate Salt of Compound 1:

The TFA salt of Compound 1 (110 mg in 20 mL of 0.5 M HOAc) was loaded onto a 30-mL AG 1×2 ion exchange resin column (acetate form, Bio-Rad Laboratories). The resin was pre-washed with water until a constant conductivity was obtained. It was eluted with 0.5 M HOAc at a 12 mL/min flow rate. The desired fractions were combined and lyophilized. Caution was taken to avoid prolonged exposure of the material to air. 90 mg of the acetate salt of Compound 1 was obtained.

EXAMPLE 2

Formulation for the Preparation of Compound 1 Complexed with $^{99m}Tc$

A solution of the TFA salt of Compound 1 synthesized as described in Example 1 was prepared at a concentration of 0.08 mg/mL in 0.05N HCl or 0.1% TFA. A pH 3 solution of gentisic acid was prepared by dissolving gentisic acid, sodium salt (Sigma) to a concentration of 100 mg/mL and the pH was adjusted to between 2.9 and 3.0 with HCl (1N). A stannous chloride solution (20 mg/mL) was prepared by dissolving $SnCl_2 \cdot 2H_2O$ in $N_2$-purged HCl (1N). A stannous gluconate solution was prepared by the addition of 20 µL of stannous chloride solution to 1 mL of sodium gluconate solution. A hydroxypropyl-γ-cyclodextrin solution (50 mg/mL) was prepared by dissolving HP-γ-CD in water. All the solvents used to prepare these solutions were purged with nitrogen.

To prepare the $^{99m}Tc$ complex of Compound 1, 300 µL of ethanol, 50 µL of ligand solution (4 µg Compound 1), 200 µL of gentisic acid solution (20 mg), 50 µL of hydroxypropyl-γ-cyclodextrin solution (2.5 mg) 100 µL of stannous gluconate solution (40 µg of $SnCl_2$), and $^{99m}TcO_4^-$ (~40 mCi) was added. Water was added to bring the final volume to 1.0 mL, and the reaction was heated at 100° C. for 15-20 min.

The $^{99m}Tc$ labeled peptide purity was determined by HPLC using a Vydac C18 protein and peptide analytical column, 300 A pore size, 4.6×250 mm column length. The following gradient (flow rate 1 mL/min) was used: Isocratic elution 78% $H_2O$ (0.1% TFA)/22% $CH_3CN$ (0.1% TFA) for 20 min, gradient from 78% to 40% $CH_3CN$ (0.1% TFA) over 5 min, hold at 40% $CH_3CN$ (0.1% TFA) for 10 min, ramp from 40% to 78% $CH_3CN$ (0.1% TFA) over 5 min.

The percentage of radiocolloid in the radiolabeled product was determined using a C18 (10×2 cm) plate eluted with 60% $CH_3CN/30\%$ $H_2O/10\%$ $NH_4OH$. A 2 µL aliquot of the reaction mixture were spotted at 1.5 cm and the plate developed up to 9.5 cm. The plates were counted on a Bioscan Radiochromatoscan, Model AR2000. The activity measured from 0 to 2 cm represents the % radiocolloid. The formulation prepared in this example had a radiochemical purity (RCP) value of ~93% at 18 minutes and 91% at 6 hours post reconstitution with 40 mCi of $^{99m}TcO_4^-$.

EXAMPLE 3

Effect of Chelating Core on RCP

The following experiment was performed to examine the effect of the chelating core on RCP. The TFA salt of Compound 1 ((NMe$_2$-Gly-Ser-Cys)-Gly-(5-aminovaleric acid)-Gln-Trp-Ala-Val-Gly-His-Leu-Met-NH$_2$) was synthesized as described in Example 1. The compounds shown in Table 2 were prepared by solid phase peptide synthesis following appropriate modification of the synthesis shown in Example 1.

TABLE 2

Structure of Additional Compounds used in Example 3

| Cmpd. No. | Structure |
|---|---|
| 2 | NMe$_2$-Gly-Gly-Cys-Gly-5-aminovaleroyl-Gln-Trp-Ala-Val-Gly-His-Leu-Met-MH$_2$ |
| 3 | NH$_2$-Gly-Ser-Cys-Gly-5-aminovalerioyl-Gln-Trp-Ala-Val-Gly-His-Leu-Met-NH$_2$ |
| 4 | NH$_2$-Gly-Gly-Cys-Gly-5-aminovaleroyl-Gln-Trp-Ala-Val-Gly-His-Leu-Met-NH$_2$ |

Solutions of Compounds 1-4 were prepared at a concentration of 0.08 mg/mL in 0.05 N HCl. A pH 3 solution of gentisic acid was prepared by dissolving gentisic acid, sodium salt (223 mg, Sigma) in water and the pH was adjusted to 3.0 with HCl (1N). The final volume of the solution was 2.79 mL. A stannous chloride solution was prepared by dissolving SnCl$_2$.2H$_2$O (1.547 mg, 0.007 mmol, Aldrich) in 500 µL of N$_2$ purged 0.05N HCl. To this solution was added 51 mg (0.23 mmol) of gluconic acid, sodium salt (Sigma) and the volume was adjusted to 2978 µL. All solvents used to prepare these solutions were purged with nitrogen.

To prepare the $^{99m}$Tc complex, 50 µL of ligand solution (4 µg Compound 1-4), 300 µL of EtOH, 250 µL of gentisic acid solution (20 mg), 50 µL of 1SnCl$_2$: 34 Gluconic acid (40 µg of SnCl$_2$), and $^{99m}TcO_4^-$ (~40 mCi, Syncor) was added. Water was added to bring the final volume to 1.0 mL, and the reaction was allowed to stand at room temperature for 15 min. The solutions were then analyzed for RCP as described in Example 2. The results are shown in Table 3.

TABLE 3

HPLC Analysis of Compounds 1-4, Average RCP Values

| Compound | Percent RCP at 15 min | Percent RCP at 6 hours | Percent Radiocolloid |
|---|---|---|---|
| 1 | 91.2 | 88.1 | 1.2 |
| 2 | 80.8 | 78.7 | 0.95 |
| 3 | 86.7 | 82.4 | 0.31 |
| 4 | 83.3 | 83.3 | 2 |

Each experiment was performed multiple times and the average is reported in Table 3.

EXAMPLE 4

Kits for the Preparation of TcOMe$_2$N-Gly-Ser-Cys-Gly-5-aminovaleroyl-Glu-Trp-Ala-Val-Gly-ylis-Leu-Met-NH$_2$ This example describes a two component kit used for the preparation of a radiopharmaceutical of the invention. As summarized in Table 4, the kit may include two vials, however the contents of Vial 2 need not be supplied with the kit.

TABLE 4

A kit for the preparation of a radiopharmaceutical formulation of the invention

| Vial 1 | Vial 2 |
|---|---|
| 4 µg Compound 1 (triflate or acetate salt) 40 µg of SnCl$_2$2H$_2$O 1.3 mg of Gluconic acid, sodium salt 20 mg of gentisic acid, sodium salt 2.5 mg of hydroxypropyl-γ-cyclodextrin (optional) pH 3-4 | 300 µL of EtOH |

Vial 1 is reconstituted with 300 µL of EtOH from Vial 2, 40 mCi of $^{99m}TcO_4^-$ is added, followed by normal saline to a final volume of 1.0 mL. The vial is then either allowed to stand at room temperature for 15 min., or heated at 100° C. for 5 to 20 min. As indicated in Table 4, the inclusion of hydroxypropyl-γ-cyclodextrin is optional.

Use of Detergent in Lyophilized Formulation

The previously described formulation developed for the syntheses of $^{99m}$Tc-COMPOUND 1 comprises 30% (300 µl) EtOH, which is utilized to improve recovery of the $^{99m}$Tc complex from the vial. If a freeze-dried kit is desired, EtOH, being a liquid, requires a two-vial formulation because it cannot be freeze-dried with the other formulation components. The use of a solid compound instead of EtOH would reduce the number of vials from two to one, thus potentially reducing production costs considerably.

Two non-ionic detergents, Cyclohexyl-n-methyl-β-D-maltoside and n-Hexyl-β-D-Glucopyranoside, were tested for this purpose.

Cyclohexyl-n-methyl-β-D-maltoside n-Hexyl-β-D-Glucopyranoside

These detergents were chosen because they should not dissolve biological membranes (they are not ionic detergents), they are very water-soluble, and they contain a sugar moiety that has potential exchange ligand properties.

EXAMPLE 5

Syntheses of $^{99m}$Tc COMPOUND 1 (No ethanol or surfactant added)

A stannous gluconate solution was prepared by dissolving 2.303 mg (0.001 mmol) of $SnCl_2.2H_2O$ in 500 µL of $N_2$-purged 0.05N HCl. To this solution was added 76 mg (0.347 mmol) of sodium gluconate and the volume was adjusted to 2.878 mL of water.

Compound 1 (275 µg, COMPOUND 1 acetate salt) was dissolved in 2.750 mL of 0.05N HCl. Gentisic acid (158.6 mg) was dissolved in water and the pH was adjusted to 3.0 using 1N HCl; the final volume was 2.08 mL.

To 50 µL of the Compound 1 solution (4 µg) was added $^{99m}TcO_4^-$ (190 µL, 41.5 mCi), 0.458 mL of $H_2O$, 50 µL of the stannous gluconate solution (40 µg of $SnCl_2$) and 262 µL of gentisic acid solution (20 mg). The reaction was heated at 100° for 5 min. prior to HPLC analysis, which was performed using the following system: Vydac C-18 Protein and Peptide column (4.6×250 mm) eluted with 78% $H_2O$ (0.1% TFA)/ 22% $CH_3CN$ (0.1% TFA) for 20', ramped from 78% to 40% $H_2O$ (0.1% TFA) in 5', held at 40% $H_2O$ (0.1% TFA) for 10', then ramped from 40% to 78% $H_2O$ (0.1% TFA) in 5'. Flow rate: 1 mL/min. The resulting RCP was 87.4% initially and 87.1% at 6 hours. The recovery from the vial was 67%.

This example shows that recovery of $^{99m}$Tc COMPOUND 1 from the vial was low in the absence of added ethanol or surfactant.

EXAMPLE 6

Syntheses of $^{99m}$Tc COMPOUND 1 with 300 µl of EtOH (no surfactant)

Stannous gluconate, Compound 1 and Gentisic acid solutions were prepared as described in Example 5. To 50 µL of the Compound 1 solution (4 µg) was added $^{99m}TcO_4^-$ (170 µL, 38.5 mCi), 0.178 mL of $H_2O$, 50 µL of the stannous gluconate solution (40 µg of $SnCl_2$), 262 µL of gentisic acid solution (20 mg) and 300 µL of EtOH. The reaction was heated and analyzed as described in Example 5. The resulting RCP ranged from 91.1 to 93.1%, and ranged from 87.0 to 90.3% at 6 hours. Radiocolloid values of 0.5 and 0.7 were observed (n=2) The recovery from the vial was 98.44% (n=1).

This example shows that recovery of $^{99m}$Tc COMPOUND 1 from the vial could be improved by substitution of EtOH for some of the water in the formulation.

EXAMPLE 7

Syntheses of $^{99m}$Tc COMPOUND 1 with 10 mg of Cyclohexyl-n-methyl-β-D-maltoside:

A stannous gluconate solution was prepared by dissolving 1.597 mg (0.007 mmol) of $SnCl_2.2H_2O$ in 500 µL of $N_2$-purged 0.05N HCl. To this solution was added 51 mg (0.233 mmol) of sodium gluconate and the volume was adjusted to 1.996 mL with water. Compound 1 (211 µg, COMPOUND 1 acetate salt) was dissolved in 2.637 mL of 0.05N HCl. Gentisic acid (238.8 mg) was dissolved in water and the pH was adjusted to 3.0 using 1N HCl; the final volume was 3.085 mL. Cyclohexyl-n-methyl-β-D-maltoside (55 mg) was dissolved in 550 µL of $H_2O$.

To 50 µL of the Compound 1 solution (4 µg) was added $^{99m}TcO_4^-$ (270 µL, 38 mCi), 0.272 mL of $H_2O$, 50 µL of the stannous gluconate solution (40 µg of $SnCl_2$), 258 µL of gentisic acid solution (20 mg) and 100 µL (10 mg) of the maltoside solution. The reaction was heated and analyzed as described in Example 5. The resulting RCP was 88.2% and the % of radiocolloid was 1.3%.

This example shows that the yield of $^{99m}$TcO COMPOUND 1 was not affected by the addition of maltoside, when compared to that obtained in its absence (Example 5).

EXAMPLE 8

Syntheses of $^{99m}$Tc COMPOUND 1 with 15 mg of Cyclohexyl-n-methyl-β-D-maltoside Stannous gluconate, Compound 1 and Gentisic acid solutions were prepared as described in Example 5. Cyclohexyl-n-methyl-β-D-maltoside (36.2 mg) was dissolved in 518 µL of $H_2O$. To 50 µL of the Compound 1 solution (4 µg) was added $^{99m}TcO_4^-$ (210 µL, 38.4 mCi), 0.338 mL of $H_2O$, 50 µL of the stannous gluconate solution (40 µg of $SnCl_2$), 262 µL of gentisic acid solution (20 mg) and 100 µL (15 mg) of the maltoside solution. The reaction was heated and analyzed as described in Example 5. The resulting RCP was 88.0% and recovery from the vial was 90.3%.

This example shows that relative to the conditions used in Example 5, recovery of $^{99m}$Tc COMPOUND 1 from the vial could be improved by addition of Cyclohexyl-n-methyl-β-D-maltoside to the vial, without adversely affecting RCP.

EXAMPLE 9

Syntheses of $^{99m}$Tc COMPOUND 1 with 50 mg of Cyclohexyl-n-methyl-β-D-maltoside Stannous gluconate, Compound 1, and gentisic acid solutions were prepared as described in Example 7. Cyclohexyl-n-methyl-β-D-maltoside (85 mg) was dissolved in 510 µL of $H_2O$. To 50 µL of the Compound 1 solution (4 µg) was added $^{99m}TcO_4^-$ (230 µL, 39.6 mCi), 0.168 mL of $H_2O$, 50 µL of the stannous gluconate solution (40 µg of $SnCl_2$), 262 µL of gentisic acid solution (20 mg) and 300 µL (50 mg) of the maltoside solution. The reaction was heated and analyzed as described in Example 5. The resulting RCP was 88.5 and 90.5%. The recovery from the vial was 95.6% (n=1).

This example shows that relative to the conditions used in Example 5, recovery of $^{99m}$Tc COMPOUND 1 from the vial could be improved by addition of Cyclohexyl-n-methyl-β-D-maltoside to the vial, without adversely affecting RCP, and that recovery was improved by the use of 50 mg of surfactant, relative to the use of 15 mg of surfactant.

EXAMPLE 10

Syntheses of $^{99m}$Tc COMPOUND 1 with 100 mg of Cyclohexyl-n-methyl-β-D-maltoside Stannous gluconate, Compound 1 and Gentisic acid solutions were prepared as described in Example 7. Cyclohexyl-n-methyl-β-D-maltoside (127.9 mg) was dissolved in 518 µL of $H_2O$. To 50 µL of the Compound 1 solution (4 µg) was added $^{99m}TcO_4^-$ (220 µL, 41.6 mCi), 0.022 mL of $H_2O$, 50 µL of the stannous gluconate solution (40 μg of SnCl$_2$), 258 μL of gentisic acid solution (20 mg) and 400 μL (10 mg) of the maltoside solution. The reaction was heated and analyzed as described in Example 5. The resulting RCP was 90%. The % of radiocolloid was 0.5%.

EXAMPLE 11

Syntheses of $^{99m}$Tc COMPOUND 1 with 10 mg of n-Hexyl-β-D-Glucopyranoside:

A stannous gluconate solution was prepared by dissolving 2.383 mg (0.001 mmol) of SnCl$_2$·2H$_2$O in 500 μL of N$_2$-purged 0.05N HCl. To this solution was added 78 mg (0.36 mmol) of sodium gluconate and the volume was adjusted to 2.978 mL with water. Compound 1 (265 μg) (acetate salt) was dissolved in 2.650 mL of 0.05N HCl. Gentisic acid (204.1 mg) was dissolved in water and the pH was adjusted to 3.0 using 1N HCl; the final volume was 2.551 mL. n-Hexyl-β-D-Glucopyranoside (180.6 mg) was dissolved in 672 μL of H$_2$O.

To 50 μL of the Compound 1 solution (4 μg) was added $^{99m}$TcO$_4^-$ (210 μL, 38 mCi), 0.41 mL of H$_2$O, 50 μL of the stannous gluconate solution (40 μg of SnCl$_2$), 250 μL of gentisic acid solution (20 mg) and 40 μL (10 mg) of the maltoside solution. The reaction was heated and analyzed as described in Example 5. The resulting RCP was 86.4% and the % of radiocolloid was 1.1%. Recovery from the vial 96.3%.

This example shows that relative to the conditions used in Example 5, recovery of $^{99m}$Tc COMPOUND 1 from the vial could be improved by addition of n-Hexyl-β-D-Glucopyranoside to the vial, without adversely affecting RCP.

EXAMPLE 12

Syntheses of $^{99m}$Tc COMPOUND 2 with 50 mg of n-Hexyl-β-D-Glucopyranoside:

Stannous gluconate, Compound 1 and Gentisic acid solutions were prepared as described in Example 11. n-Hexyl-β-D-Glucopyranoside (180.6 mg) was dissolved in 672 μL of H$_2$O.

To 50 μL of the Compound 1 solution (4 μg) was added $^{99m}$TcO$_4^-$ (160 μL, 41 mCi), 0.3 mL of H$_2$O, 50 mL of the stannous gluconate solution (40 μg of SnCl$_2$), 250 μL of gentisic acid solution (20 mg) and 200 μL (50 mg) of the maltoside solution. The reaction was heated and analyzed as described in Example 5. The resulting RCP was 92.7% initially, and 89.1% at 6 hours. The % of radiocolloid was 1.2% and the recovery from the vial 98.8%. A representative chromatogram is shown below.

SUMMARY

As it is shown in the following table the recoveries obtained using these detergents are very similar to the ones in which EtOH was used. Moreover the RCP obtained with n-Hexyl-β-D-Glucopyranoside are comparable to the ones with EtOH.

| Detergent | Initial RCP (%) | RCP 6 h (%) | Colloids (%) | Recovery (%) |
|---|---|---|---|---|
| No EtOH | 87.4 | 87.1 | | 67.0 |
| EtOH | 93.1 | 88.2 | | 98.4 |
| EtOH | 92.5 | 90.3 | 0.7 | |
| EtOH | 91.1 | 87.0 | 0.5 | 98.6 |
| 10 mg maltoside | 88.2 | | 1.3 | |
| 15 mg maltoside | 88.0 | | | 90.3 |
| 50 mg maltoside | 88.5 | | | 95.6 |
| 50 mg maltoside | 90.5 | 85.2 | 1 | |
| 100 mg maltoside | 90.0 | | 0.5 | |
| 10 mg Glucopyranoside | 86.4 | | 1.1 | 96.3 |
| 50 mg Glucopyranoside | 90.8 | | 0.4 | |
| 50 mg Glucopyranoside | 92.7 | 89.1 | 1.2 | 98.8 |

OTHER EMBODIMENTS

From the foregoing description, it will be apparent that variations and modifications may be made to the invention described herein to adopt it to various usages and conditions.

INCORPORATION BY REFERENCE

All publications, patents, and patent applications mentioned in this specification are herein incorporated by reference to the same extent as if each independent publication, patent, or patent application was specifically and individually indicated to be incorporated by reference.

What is claimed is:

1. A radiopharmaceutical composition comprising:
a compound of Formula 1a a reducing agent;
an exchange ligand;
a stabilizer;
a detergent;
a diluent; and
a radionuclide,
wherein
L is optional and is a linking group;
Z is a targeting molecule; and
wherein the compound of Formula 1a is present at less than 10 µg per mL of diluent.

2. A composition for the preparation of a radiopharmaceutical comprising:

a compound of Formula 1a a reducing agent;
an exchange ligand;
a stabilizer; and
a detergent
wherein
L is optional and is a linking group;
Z is a targeting molecule, and wherein the compound of Formula 1a is present in an amount such that the resulting radiopharmaceutical contains less than 10 µg per mL of diluent.

3. A composition of any one of claims 1 or 2 wherein Z is a bombesin analog.

4. A composition of claim 3 wherein Z is selected from the group consisting of SEQ ID NO:1; SEQ ID NO:2; SEQ ID NO:3; SEQ ID NO:4; SEQ ID NO:5; SEQ ID NO:6; and SEQ ID NO:7.

5. A radiopharmaceutical composition comprising:
a compound of Formula 2

Formula 2 a reducing agent;
an exchange ligand;
a stabilizer;
a detergent;
a diluent; and
a radionuclide, wherein the compound of Formula 2 is present at less than 10 μg per mL of diluent.

6. A composition for the preparation of a radiopharmaceutical comprising:
a compound of Formula 2

Formula 2 a reducing agent;
an exchange ligand; and
a stabilizer; and
a detergent, wherein the compound of Formula 2 is present in an amount such that the resulting radiopharmaceutical contains less than 10 μg per mL of a diluent.

7. A composition of any one of claims 2 or 6 wherein the reducing agent is selected from the group consisting of stannous salt, sodium borohydride, cupric salts, and formamidine sulfinic acid.

8. A composition of any one of claims 2 or 6 wherein the exchange ligand is selected from the group consisting of gluconate, gentisic acid and glucoheptonate.

9. A composition of any one of claims 2 or 6 wherein the stabilizer is selected from the group consisting of gentisic acid, maltose and ascorbic acid.

10. A composition of any one of claims 2 or 6 further comprising a solubilizer.

11. A composition of claim 10, wherein the solubilizer is a cyclodextrin.

12. A composition of claim 11, wherein the solubilizer is hydroxypropyl-γ-cyclodextrin.

13. A composition of any one of claims 1 or 5 wherein the diluent is selected from the group consisting of ethanol, water and saline.

14. A radiopharmaceutical composition comprising:
a compound of Formula 2

Formula 2 stannous chloride;
gluconic acid;
gentisic acid;
ethanol; and
a radionuclide, wherein the compound of formula 2 is present at less than 10 μg per mL of diluent.

15. A composition for the preparation of a radiopharmaceutical comprising:
a compound of Formula 2, Formula 2 stannous chloride;
gluconic acid; and
gentisic acid, wherein the compound of Formula 2 is present in an amount such that the resulting radiopharmaceutical contains less than 10 μg per mL of a diluent.

16. A composition of claim 15, further comprising hydroxypropyl-γ-cyclodextrin.

17. A radiopharmaceutical composition of claim 1, wherein the compound of Formula 1 is present at less than 5 μg per mL of diluent.

18. A radiopharmaceutical composition of any one of claims 1 or 5, wherein the radiopharmaceutical is prepared and administered to a subject without purification.

19. A radiopharmaceutical composition of any one of claims 1 or 5, wherein the RCP of the composition is greater than or equal to about 90% at about 15 minutes.

20. A composition of any one of claims 2 or 6, wherein the compound of Formula 1 is present in an amount such that the resulting radiopharmaceutical contains less than 5 μg per mL of diluent.

21. A composition of any one of claims 2 or 6, wherein the resulting radiopharmaceutical is prepared and administered to a subject without purification.

22. A composition of any one of claims 2 or 6, wherein the RCP of the resulting radiopharmaceutical is greater than or equal to about 90% at about 15 minutes.

23. A composition of claim 15, further comprising a detergent.

24. A composition of claim 15, further comprising a detergent, wherein the composition is in lyophilized form.

25. A composition of any one of claims 2, 6, or 15 further comprising a diluent, optionally contained in a separate container.

26. The radiopharmaceutical of claim 14 further comprising a detergent.

27. The radiopharmaceutical of any one of claims 1, 5 or 26 wherein the detergent is selected from the group consisting of non-ionic, cationic and zwitterionic surfactants.

28. The composition of any one of claims 2, 6 or 23 wherein the detergent is selected from the group consisting of non-ionic, cationic and zwitterionic surfactants.

29. The radiopharmaceutical of any one of claims 1, 5 or 26 wherein the detergent is a non-ionic detergent.

30. The composition of any one of claims 2, 6 or 23, wherein the detergent is selected from the group consisting of cyclo-n-methyl-β-D-maltoside and n-hexyl-β-D-glucopyranoside.

31. The radiopharmaceutical of any one of claims 1, 5 or 26, wherein the detergent is selected from the group consisting of cyclo-n-methyl-β-D-maltoside and n-hexyl-β-D-glucopyranoside.

* * * * *

SEQUENCE LISTING

<160> NUMBER OF SEQ ID NOS: 7

<210> SEQ ID NO 1
<211> LENGTH: 14
<212> TYPE: PRT
<213> ORGANISM: Artificial
<220> FEATURE:
<223> OTHER INFORMATION: Description of Artificial Sequence: Synthetic
      Peptide
<220> FEATURE:
<221> NAME/KEY: MOD_RES
<222> LOCATION: (1)..(1)
<223> OTHER INFORMATION: Pyroglutamic acid
<220> FEATURE:
<221> NAME/KEY: MOD_RES

```
<222> LOCATION: (14)..(14)
<223> OTHER INFORMATION: Aminated Methionine

<400> SEQUENCE: 1

Glu Gln Arg Leu Gly Asn Gln Trp Ala Val Gly His Leu Met
1               5                   10

<210> SEQ ID NO 2
<211> LENGTH: 14
<212> TYPE: PRT
<213> ORGANISM: Artificial
<220> FEATURE:
<223> OTHER INFORMATION: Description of Artificial Sequence: Synthetic
      Peptide
<220> FEATURE:
<221> NAME/KEY: MOD_RES
<222> LOCATION: (1)..(1)
<223> OTHER INFORMATION: Pyroglutamic acid
<220> FEATURE:
<221> NAME/KEY: MOD_RES
<222> LOCATION: (14)..(14)
<223> OTHER INFORMATION: Aminated Methionine

<400> SEQUENCE: 2

Glu Gly Arg Leu Gly Thr Gln Trp Ala Val Gly His Leu Met
1               5                   10

<210> SEQ ID NO 3
<211> LENGTH: 27
<212> TYPE: PRT
<213> ORGANISM: Artificial
<220> FEATURE:
<223> OTHER INFORMATION: Description of Artificial Sequence: Synthetic
      Peptide
<220> FEATURE:
<221> NAME/KEY: MOD_RES
<222> LOCATION: (27)..(27)
<223> OTHER INFORMATION: Aminated Methionine

<400> SEQUENCE: 3

Val Pro Leu Pro Ala Gly Gly Gly Thr Val Leu Thr Lys Met Tyr Pro
1               5                   10                  15

Arg Gly Asn His Trp Ala Val Gly His Leu Met
            20                  25

<210> SEQ ID NO 4
<211> LENGTH: 9
<212> TYPE: PRT
<213> ORGANISM: Artificial
<220> FEATURE:
<223> OTHER INFORMATION: Description of Artificial Sequence: Synthetic
      Peptide
<220> FEATURE:
<221> NAME/KEY: MOD_RES
<222> LOCATION: (1)..(1)
<223> OTHER INFORMATION: Pyroglutamic acid
<220> FEATURE:
<221> NAME/KEY: MOD_RES
<222> LOCATION: (9)..(9)
<223> OTHER INFORMATION: Aminated Methionine

<400> SEQUENCE: 4

Glu Gln Trp Ala Val Gly His Phe Met
1               5

<210> SEQ ID NO 5
<211> LENGTH: 11
<212> TYPE: PRT
<213> ORGANISM: Artificial
<220> FEATURE:
```

```
<223> OTHER INFORMATION: Description of Artificial Sequence: Synthetic
      Peptide
<220> FEATURE:
<221> NAME/KEY: MOD_RES
<222> LOCATION: (1)..(1)
<223> OTHER INFORMATION: Pyroglutamic acid
<220> FEATURE:
<221> NAME/KEY: MOD_RES
<222> LOCATION: (11)..(11)
<223> OTHER INFORMATION: Aminated Methionone

<400> SEQUENCE: 5

Glu Val Pro Gln Trp Ala Val Gly His Phe Met
1               5                   10

<210> SEQ ID NO 6
<211> LENGTH: 32
<212> TYPE: PRT
<213> ORGANISM: Artificial
<220> FEATURE:
<223> OTHER INFORMATION: Description of Artificial Sequence: Synthetic
      Peptide
<220> FEATURE:
<221> NAME/KEY: MOD_RES
<222> LOCATION: (32)..(32)
<223> OTHER INFORMATION: Aminated Methionine

<400> SEQUENCE: 6

Ala Pro Leu Ser Trp Asp Leu Pro Glu Pro Arg Ser Arg Ala Ser Lys
1               5                   10                  15

Ile Arg Val His Ser Arg Gly Asn Leu Trp Ala Thr Gly His Phe Met
            20                  25                  30

<210> SEQ ID NO 7
<211> LENGTH: 9
<212> TYPE: PRT
<213> ORGANISM: Artificial
<220> FEATURE:
<223> OTHER INFORMATION: Description of Artificial Sequence: Synthetic
      Peptide
<220> FEATURE:
<221> NAME/KEY: MOD_RES
<222> LOCATION: (1)..(1)
<223> OTHER INFORMATION: Pyroglutamic acid
<220> FEATURE:
<221> NAME/KEY: MOD_RES
<222> LOCATION: (9)..(9)
<223> OTHER INFORMATION: Aminated Methionine

<400> SEQUENCE: 7

Glu Leu Trp Ala Val Gly Ser Phe Met
1               5
```